United States Patent [19]

Aggarwal et al.

[11] Patent Number: 5,795,967
[45] Date of Patent: Aug. 18, 1998

[54] TUMOR NECROSIS FACTOR ANTAGONISTS AND THEIR USE

[75] Inventors: Bharat B. Aggarwal; Michael A. Palladino, both of San Mateo; Mohamed R. Shalaby, San Rafael, all of Calif.

[73] Assignee: Genentech, Inc., South San Francisco, Calif.

[21] Appl. No.: 482,226

[22] Filed: Jun. 7, 1995

Related U.S. Application Data

[63] Continuation of Ser. No. 342,676, Nov. 21, 1994, abandoned, which is a continuation of Ser. No. 174,212, Dec. 28, 1993, abandoned, which is a continuation of Ser. No. 26,717, Mar. 5, 1993, abandoned, which is a continuation of Ser. No. 707,412, May 28, 1991, abandoned, which is a continuation of Ser. No. 417,171, Oct. 4, 1989, abandoned, which is a continuation of Ser. No. 898,272, Aug. 20, 1986, abandoned, which is a continuation-in-part of Ser. No. 754,507, Jul. 12, 1985, abandoned, and Ser. No. 881,311, Jul. 2, 1986, abandoned, which is a continuation-in-part of Ser. No. 677,156, Dec. 3, 1984, abandoned, which is a continuation-in-part of Ser. No. 627,959, Jul. 5, 1984, abandoned.

[51] Int. Cl.$^6$ .............................. C07K 16/00; C12N 5/06; A61K 39/395
[52] U.S. Cl. ........................ 530/388.23; 530/388.2; 530/388.4; 530/387.1; 530/866; 435/335; 424/133.1; 424/145.1
[58] Field of Search ...................... 424/130.1, 141.1, 424/133.1, 134.1, 139.1, 158.1; 530/387.1, 388.23, 388.2, 388.4, 387.9, 387.3, 866; 435/240.27

[56] References Cited

U.S. PATENT DOCUMENTS

| | | |
|---|---|---|
| 4,338,397 | 7/1982 | Gilbert et al. . |
| 4,359,415 | 11/1982 | Sloane . |
| 4,411,994 | 10/1983 | Gilbert et al. . |
| 4,447,355 | 5/1984 | Sakamoto . |
| 4,457,916 | 7/1984 | Hayashi et al. . |
| 4,481,137 | 11/1984 | Ohnishi et al. . |
| 4,485,038 | 11/1984 | Chadha et al. . |
| 4,495,282 | 1/1985 | Ohnishi et al. . |
| 4,544,546 | 10/1985 | Wang et al. . |
| 4,677,063 | 6/1987 | Mark et al. . |
| 4,677,064 | 6/1987 | Mark et al. . |
| 4,677,197 | 6/1987 | Lin et al. . |
| 4,752,575 | 6/1988 | Granger et al. . |
| 4,758,549 | 7/1988 | Mitsuhashi et al. . |
| 4,879,226 | 11/1989 | Wallace et al. . |
| 5,118,500 | 6/1992 | Hanel et al. . |
| 5,288,852 | 2/1994 | Yamada et al. . |
| 5,654,407 | 8/1997 | Boyle et al. . |
| 5,672,347 | 9/1997 | Aggarwal et al. ............. 424/139.1 |
| 5,698,419 | 12/1997 | Wolpe et al. . |

FOREIGN PATENT DOCUMENTS

| | | |
|---|---|---|
| 086475 | 8/1983 | European Pat. Off. . |
| 087087 | 8/1983 | European Pat. Off. . |
| 090892 | 10/1983 | European Pat. Off. . |
| 100641 | 2/1984 | European Pat. Off. . |
| 131789 | 1/1985 | European Pat. Off. . |
| 132125 | 1/1985 | European Pat. Off. . |
| 134923 | 3/1985 | European Pat. Off. . |
| 146026 | 6/1985 | European Pat. Off. . |
| 148311 | 7/1985 | European Pat. Off. . |
| 155190 | 9/1985 | European Pat. Off. . |
| 155549 | 9/1985 | European Pat. Off. . |
| 158286 | 10/1985 | European Pat. Off. . |
| 168214 | 1/1986 | European Pat. Off. . |
| 3421731 | 12/1985 | Germany . |
| 186994 | 10/1984 | Japan . |
| 656 623 | 7/1986 | Switzerland . |
| 2094833 | 9/1982 | United Kingdom . |
| 2106117 | 4/1983 | United Kingdom . |
| 2117385 | 10/1983 | United Kingdom . |
| 2130219 | 5/1984 | United Kingdom . |

OTHER PUBLICATIONS

Lerner, Richard A., Nature, 299: 592–596, Oct. 1982.
Sevier, E. D. et al., Clin Chem, 27(11): 1797–1806, 1981.
Williamson, B. D. et al, PNAS, 80: 5397–5401, Sep. 1983.
Haidaris, C.G. et al., Inf. & Immun, 42(1): 385–393, Oct. 1983.
Adams et al., "Effector Mechanisms of Cytolytically Activated Macrophages" *J. of Immunology* 124(1):293–300 (1980).
Adelman et al., "In Vitro Deletional Mutagenesis for Bacterial Production of the 20,000–Dalton Form of Human Pituitary Growth Hormone" *DNA* 2(3):183–193 (1983).
Aggarwal et al., "Chemical and Biological Properties of Human Lymphotoxin" *Thymic Hormones & Lymphokines*, Goldstein, Plenum Publishing pp. 235–245 (1984).
Aggarwal et al., "Human Tumor Necrosis Factor" *Journal of Biological Chemistry* 260(4):2345–2354 (1985).
Aggarwal et al., "Human tumor necrosis factor. Production, purification, and characterization" *Chemical Abstracts* 102(15):130173u (1985).
Aksamit et al., "Macrophage cell lines produce a cytotoxin" *J. Immunol.* 122(5):1785–1790 (1979).
Armstrong et al., "Isolation and Initial Characterization of Tumoricidal Monokine(s) From the Human Monocytic Leukemia Cell Line THP-1" *JNCI* 74(1):1–9 (Jan. 1985).
Benton et al., "Screening λgt recombinant clones by hybridization to single plaques in situ" *Science* 196(4286):180–182 (1977).

(List continued on next page.)

*Primary Examiner*—Susan A. Loring
*Attorney, Agent, or Firm*—Diane L. Marschang

[57] ABSTRACT

Tumor necrosis factor antagonists are administered in therapeutically effective doses to suppress inflammatory immune-potentiated events. The antagonists of this invention typically are selected from among several classes but preferably are neutralizing antibodies directed against tumor necrosis factor. The antagonists are useful in suppressing transplantation immunity and in the treatment of autoimmune diseases.

15 Claims, No Drawings

OTHER PUBLICATIONS

Beutler et al., "Cachectin and Tumor Necrosis Factor as Two Sides of the Same Biological Coin" *Nature* 320:584–588 (Apr. 17, 1986).

Beutler, B. et al., "Identity of tumor necrosis factor and the macrophage–secreted factor cachectin" *Nature* 316:552–554 (1985).

Beutler, B. et al., "Passive Immunization Against Cachectin/Tumor Necrosis Factor Proteins Mice from Lethal Effect of Endotoxin" *Science* 229:869–871 (1985).

Birnboim and Doly, "A Rapid Alkaline Extraction Procedure for Screening Recombinant Plasmid DNA" *Nucleic Acids Research* 7:1513–1523 (1980).

Broxmeyer et al., "The Suppressive Influences of Human Tumor Necrosis Factors on Bone Marrow Hematopoietic Progenitor Cells From Normal Donors and Patients with Leukemia: Synergism of Tumor Necrosis Factor and Interferon–γ" *Journal of Immunology* 136(12):4487–4495 (Jun. 15, 1986).

Buessow et al., "Tumoricidal activity of an acute promyelocytic leukemia cell line (HL–600) is augmented by human interferon α" *Leukemia Research* 8(5):801–811 (1984).

Carswell et al., "An Endotoxin–induced Serum Factor That Causes Necrosis of Tumors" *Proc. Natl. Acad. Sci. USA* 72(9):3666–3670 (1975).

Cerletti et al., "Lymphotoxin from the human lymphoblastoid cell line LuK II: Isolation, characterization and N–terminal sequence determination" *Lymphokine Research* 6:Abstract 1452 (1987).

Cross et al., "Stimulation of polymorphonuclear leukocyte bactericidal activity by supernatants of activated human mononuclear cells" *Infection and Immunity* 22(2):502–507 (1978).

De St. Groth et al., "Production of Monoclonal Antibodies: Strategy and Tactics" *J. Immunol. Methods* 35:1–21 (1980).

Degliantoni et al., "Natural Killer (NK) Cell–Derived Hematopoietic Colony–Inhibiting Activity and NK Cytotoxic Factor" *Journal of Experimental Medicine* 162:1512–1530 (1985).

Dinarello et al., "Tumor necrosis factor (cachectin) is an endogenous pyrogen and induces production of interleukin 1" *Journal of Experimental Medicine* 163(6):1433–1450 (1986).

Evans, "Lymphotoxin–An Immunologic Hormone with Anticarcinogenic and Antitumor Activity" *Cancer Immunol. Immunother.* 12:181–190 (1982).

Ezekowitz et al., "Interaction of human monocytes, macrophages, and polymorphonuclear leukocytes with zymosan in vitro. Role of type 3 complement receptors and macrophage–derived complement" *J. Clin. Invest.* 76(6):2368–2376 (1985).

Fisch et al., "In vitro production of rabbit macrophage tumor and cytotoxin" *Chemical Abstracts* 99:137978p (1983).

Flick et al., "Tumor Necrosis Factor" *Biological Response Modifiers*, Torrence, P. (ed.), Chapter 8, pp. 171–218 (1985).

Fujiwara et al., "Increased Interleukin–1 Production and Monocyte Suppressor Cell Activity Assosiated with Human Tuberculosis" *Am. Rev. Respir. Dis.* 133:73–77 (1986).

Gamble et al., "Stimulation of the adherence of neutrophils to umbilical vein endothelium by human recombinant tumor necrosis factor" *Proc. Natl. Acad. Sci.* 82(24):8667–8671 (1985).

Granger et al., "The Human LT System. I. Physical–chemical Heterogeneity of LT Molecules Released by Mitogen Activated Human Lymphocytes In Vitro" *Cellular Immunology* 38(2):388–402 (Jul. 1978).

Granger et al., "LT Molecules form a Subunit System for Cell Toxins" *Biochemical Characterization of Lymphokines*, De Weck et al. (eds.) pp. 279–283 (1980).

Granger et al., "Receptor and Non–receptor Associated, Lymphocyte–derived Cell–lytic Molecules" *Cellular Responses to Molecular Modulators*, Mozes et al. (eds.) pp. 287–310 (1981).

Gray et al., "Cloning and Expression of cDNA for Human Lymphotoxin, a Lymphokine with Tumor Necrosis Activity" *Nature* 312:721–724 (1984).

Green et al., "*Corynebacterium parvum* as the Priming Agent in the Production of Tumor Necrosis Factor in the Mouse" *JNCI* 59(5):1519–1522 (1977).

Green et al., "Evidence for the presence of an antitumor factor in serum of normal animals" *Cancer Letters* 6:235–240 (1979).

Green et al., "Human–serum factor inhibits human tumors in vitro and in vivo," *Journal of Cell Biology* 79:67 #CU306 (1978).

Green et al., "Murine Tumor Necrosis–Inducing Factor: Purification and Effects of Myelomonocytic Leukemia Cells" *JNCI* 68(6):997–1003 (1982).

Green et al., "Partial purification of a serum factor that causes necrosis of tumors" *Proc. Natl. Acad. Sci.* 73(2):381–385 (1976).

Green et al., "A protein fraction (NHG) from serum of normal humans which is cytotoxic for HELA cells in culture" *Cancer Letters* 11:345–350 (1981).

Haidaris, C.G. et al., "Serum Containing Tumor Necrosis Factor is Cytotoxic for the Human Malaria Parasite *Plasmodium falciparum*" *Infection and Immunity* 42(1):385–393 (1983).

Hall et al., "Induction of Cytotoxic Effector Activity in the HL–60 Promyelocytic Cell Line by Incubation with Phorbol Myristate Acetate: A Model System of Human Spontaneous Monocyte–Mediated" *Cellular Immunology* 76:58–68 (1983).

Hammerstrom, "Soluble Cytostatic Factor(s) Released from Human Monocytes" *Scand. J. Immunol.* 15:311–318 (1982).

Haranaka & Satomi, "Cytotoxic Activity of Tumor Necrosis Factor (TNF) on Human Cancer Cells in vitro" *Japan J. Exp. Med.* 51(3):191–194 (1981).

Helson et al., "Effect of tumor necrosis factor on cultured human melanoma cells" *Nature* 258:731–732 (1975).

Helson et al., "Effects of murine tumor necrosis factor on heterotransplanted human tumors" *Expl. Cell Biol.* 47:53–60 (1979).

Itakura et al., "Expression in *Escherichia coli* of a Chemically Synthesized Gene for the Hormone Somatostatin" *Science* 198:1056–1063 (1977).

Johnson et al., "Lymphotoxin formation by lymphocytes and muscle in polymyositis" *J. Clin. Invest.* 51(9):2435–2449 (1972).

Klein and Park, "Graft–Versus–Host Reaction Across Different Regions of the H–2 Complex of the Mouse" *Journal of Experimental Medicine* 137:1213–1225 (1973).

Klostergaard et al., "Purification of Human α–light Class Lymphotoxin to Electrophoretic Homogeneity" *Molecular Immunology* 18(12):1049–1054 (1981).

Kniep et al., "Partial purification and chemical characterization of macrophage cytotoxicity factor (MCF, MAF) and its separation from migration inhibitory factor (MIF)" *J. Immunol.* 127(2):417–422 (1981).

Korsmeyer et al., "Differential specificity of lymphocytotoxins from patients with systemic *lupus erythematosus* and inflammatory bowel disease" *Clin. Immun. and Immunopathology* 5:67–73 (1976).

Krane et al., "Interactions among Lymphocytes, Monocytes, and Other Synovial Cells in the Rheumatoid Synovium" *Lymphokines* 7:75–136 (1982).

Kull et al., "Necrosin: Purification and properties of a cytotoxin derived from a murine macrophage–like cell line" *Proc. Natl. Acad. Sci.* 81:7932–7936 (1984).

Kull et al., "Preliminary Characterization of the Tumor Cell Cytotoxin in Tumor Necrosis Serum" *J. Immunol.* 126(4):1279–1283 (Apr. 1981).

Lerner, R.A., "Tapping the Immunological Repertoire to Produce Antibodies of Predetermined Specificity" *Nature* 299:592–596 (Oct. 1982).

Lomnitzer et al., "The Effect of PHA–Activated MN–Cell Supernatants on Polymorphonuclear Leucocyte Function" *Clin. Exp. Immunol.* 29:501–508 (1977).

Lowry et al., "Immune mechanisms in organ allograft rejection. VI. Delayed–type hypersensitivity and lymphotoxin in experimental renal allograft rejection" *Transplantation* 40(2):183–188 (1985).

Macfarlan et al., "A soluble cytotoxic factor from macrophages" *AJEBAK* 58(5):489–500 (1980).

Mannel et al., "Generation and Characterization of Lipopolysaccharide–Induced and Serum–Derived Cytotoxic Factor for Tumor Cells" *Infection and Immunity* 28(1):204–211 (1980).

Mannel et al., "Macrophages as a Source of Tumoricidal Activity (Tumor–Necrotizing Factor)" *Infection and Immunity* 30(2):523–530 (1980).

Matthews, "Tumour Necrosis Factor from the Rabbit: III. Relationship to Interferons" *Br. J. Cancer* 40:534–539 (1979).

Matthews, "Tumour–Necrosis Factor from the Rabbit: I. Mode of Action, Specificity and Physicochemical Properties" *Br. J. Cancer* 38:302–309 (1978).

Matthews et al., "Tumor–Necrosis Factor from the Rabbit. IV. Purification and Chemical Characterization" *Br. J. Cancer* 42:416–422 (1980).

Matthews, N., "Production of an anti-tumor cytotoxin by human monocytes" *Immunology* 44:135–142 (1981).

Messing et al., "A New Pair of M13 Vectors for Selecting Either DNA Strand of Double–Digest Restriction Fragments" *Gene* 19:269–276 (1982).

Mirrakhimov et al., "[Autoimmune reactions to myoglobin in myocardial infarct patients]. [Russian]" *Ter. Arkh.* (English Abstract Included) 56(10):53–56 (1985).

Mitsuhashi et al., "Target cell lysis factor and its use in cancer treatment" *Chemical Abstracts* 98(24):204393p (1983).

Moriya et al., "Antitumor effect of bacterial lipopolysaccharide (LPS) alone and in combination with Lentinian on MH–134 tumors in C3H/He mice" *Chemical Abstracts* 100(19):150731m (1984).

Murphy et al., "Gamma interferon and lymphotoxin, released by activated T cells, synergize to inhibit granulocyte/monocyte colony formation" *Journal of Experimental Medicine* 164(1):263–279 (Jul. 1, 1986).

Nawroth et al., "Modulation of endothelial cell hemostatic properties by tumor necrosis factor" *Journal of Experimental Medicine* 163(3):740–745 (1986).

Nawroth et al., "Tumor necrosis factor/cachectin interacts with endothelial cell receptors to induce release of interleukin 1" *Journal of Experimental Medicine* 163(6):1363–1375 (1986).

Nedwin et al., "Effect of Interleukin 2, Interferon–γ, and Mitogens on the Production of Tumor Necrosis Factors α and β" *J. Immunol.* 135:2492–2497 (1985).

Neumann et al., "Purification and Physicochemical Characterization of a Human Cytotoxic Factor Produced by a Human Haemic Cell Line" *Biochemical Journal* 194(3):847–856 (1981).

Nissen–Meyer et al., "Physicochemical Characterization of Cytostatic Factors Released from Human Monocytes" *Infection and Immunity* 38(1):67–73 (1982).

Oettgen et al., "Endotoxin–Induced Tumor Necrosis Factor" *Recent Results Cancer Res.* 75:207–212 (1980).

Olsson et al., "Isolation and Characterization of a T Lymphocyte–Derived Differentiation Inducing factor for the Myeloid Leukemic Cell Line HL–60" *Blood* 63(3):510–517 (1984).

Orr et al., "Purification and peptide characterization of human α–lymphotoxin obtained from the continuous human lymphoblastoid cell line IR 3.4." *Lymphokine Research* 3(4):264 (1984).

Papermaster et al., "Lymphokine Adjuvant Therapy: Bioassay of Human Lymphokine Fractions in a Mouse Tumor Model" *Human Lymphokines*, Khan et al. (eds.) pp. 459–477 (1982).

Pennica et al., "Cloning and Expression in *Escherichia Coli* of the cDNA for Murine Tumor Necrosis Factor" *Proc. Natl. Acad. Sci. USA* 82:6060–6064 (Sep. 1985).

Pennica et al., "Human Tumor Necrosis Factor: Precursor Structure, Expression and Homology to Lymphotoxin" *Nature* 312:724–729 (1984).

Peter et al., "Comparison of Cytotoxins from Joint Fluid with Lymphocyte–Produced Cytotoxins and Their Inhibition by Antiinflammatory Drugs" *Arthritis Rheum.* 14:179–180 (1971).

Peter., "Cytotoxin(s) produced by human lymphocytes: inhibition by anti–inflammatory steroids and anti–malarial drugs" *Cellular Immunology* 2:199–202 (1971).

Pichyangkul, N.O. et al., "Purification of Lymphotoxin from RPMI–1788 Cell Line Supernate" *Human Lymphokines*, Khan et al. (eds.) pp. 173–183 (1982).

Picken et al., "Nucleotide sequence of the gene for heat-–stable exterotoxin II of *Escherichia coli*" *Infection and Immunity* 42(1):269–275 (1983).

Powell et al., "The Differential Inhibitory Effect of Lymphotoxin and Immune Interferon on Normal and Malignant Lymphoid Cells" *Lymphokine Research* 4(1):13–26 (1985).

Richey, J., "FPLC: A comprehensive separation technique for biopolymers" *American Laboratory* (Oct. 1982).

Rubin et al., "High–affinity Binding of $^{125}$I–labeled Human Tumor Necrosis Factor (LuKII) to Specific Cell Surface Receptors" *Journal of Experimental Medicine* 162:1099–1104 (Sep. 1985).

Rubin et al., "Purification and Characterization of a Human Tumor Necrosis Factor from the LuKII Cell Line" *Proc. Natl. Acad. Sci. USA* 82:6637–6641 (Oct. 1985).

Ruddle, "Lymphotoxin Production in AIDS" *Immunology Today* 7:8–9 (1986).

Ruddle et al., "Lymphotoxin, a Biologically Relevant Model Lymphokine" *Lymphokine Research* 2(1):23–31 (1983).

Ruff et al., "Purification and physico-chemical characterization of rabbit tumor necrosis factor" *Chemical Abstracts* 93(19):184125u (1980).

Ruff et al., "Tumor Necrosis Factor" *Lymphokines* 2:235–272 (1981).

Sanderson et al., "A Lymphocyte Growth Factor Made by a Human Lymphoid Cell Line" *Immunol. Rev.* 51:177–191 (1980).

Satomi et al., "Research on the Production Site of Tumor Necrosis Factor (TNF)" *Japan J. Exp. Med.* 51(6):317–322 (1981).

Sevier et al., "Monoclonal Antibodies in Clinical Immunology" *Clinical Chemistry* 27(11):1797–1806 (1981).

Shalaby et al., "Activation of Human Polymorphonuclear Neutrophil Functions by Interferon-γ and Tumor Necrosis Factors" *J. Immunol.* 135(3):2069–2073 (Sep. 1985).

Shalaby et al., "Bacteria-Derived Human Leukocyte Interferons Alter in Vitro Humoral and Cellular Immune Responses" *Cellular Immunology* 82:269–281 (1983).

Simonsen et al. *Biological Problems of Grafting*, F. Albert et al. (eds.), Charles C. Thomas pp. 214–238 (1959).

Stahli et al., "High Frequencies of Antigen–Specific Hybridomas: Dependence on Immunization Parameters and Prediction by Spleen Cell Analysis" *J. Immunological Methods* 32:297–304 (1980).

Stolpen et al., "Recombinant tumor necrosis factor and immune interferon act singly and in combination to reorganize human vascular endothelial cell monolayers" *Am. J. Pathol.* 123(1):16–24 (1986).

Stone–Wolff et al., "Interrelationships of Human Interferon-γ with Lymphotoxin and Monocyte Cytotoxin" *Journal of Experimental Medicine* 159:828–843 (Mar. 1984).

Strickland et al., "Serum lymphocytotoxins in inflammatory bowel disease. Studies of frequency and specificity for lymphocyte subpopulations" *Clin. Exp. Immunol.* 21:384–393 (1975).

Takeda et al., "Identity of Differentiation Inducing Factor and Tumour Necrosis Factor" *Nature* 323:338–340 (Sep. 25, 1986).

Terasaki et al., "Cytotoxins in disease. Autocytotoxins in lupus" *New Engl. J. Med.* 283(14):724–728 (1970).

Toth et al., "The Human Lymphotoxin System–VI. Identification of Various Saccharides on LT Molecules and Their Contribution to Cytotoxicity and Charge Heterogeneity" *Molecular Immunology* 16:671–679 (1979).

Trivers et al., "Mouse Lymphotoxin" *J. of Immunology* 117(1):130–135 (1976).

Uemura et al, "Purification and Characterization of Tumor Generating Factor" *Igaku No Ayumi* (Translation) 129(4):237–238 (1984).

Uemura et al., "Purification and characterization of tumor generating factor" *Chemical Abstracts* 101(5):036803g (1984).

Ugelstad et al., "Monodisperse polymer particles–a step forward for chromatography" *Nature* 303:95–96 (1983).

Umeda et al., "Cytotoxic effect of tumor necrosis factor on human lymphocytes and specific binding of the factor to the target cells" *Cellular and Molecular Biology* 29(5):349–352 (1983).

Wanebo et al., "Antitumor Effects of a Normal Human Serum Factor (Normal Human Globulin Fraction 1) on Human Tumor Cells In Vitro" *JNCI* 72(3):545–555 (1984).

Williamson et al., "Human Tumor Necrosis Factor Produced by Human B–cell Lines: Synergistic Cytotoxic Interaction with Human Interferon" *Proc. Natl. Acad. Sci. USA* 80:5397–5401 (Sep. 1983).

Wright et al., "Studies on the mechanism of natural killer cytotoxicity" *J. of Immunology* 130(5):2479–2483 (1983).

Zacharchuk et al., "Macrophage–mediated Cytotoxicity: Role of a Soluble Macrophage Cytotoxic Factor Similar to Lymphotoxin and Tumor Necrosis Factor" *Proc. Natl. Acad. Sci. USA* 80:6341–6345 (1983).

TUMOR NECROSIS FACTOR ANTAGONISTS AND THEIR USE

This is a continuation of application(s) Ser. No. 08/342,676 filed on 21 Nov. 1994, now abandoned, which is a continuation application of Ser. No. 08/174,212 filed on 28 Dec. 1993, now abandoned, which is continuation application of Ser. No. 08/026,717 filed on 5 Mar. 1993, now abandoned, which is a continuation application of Ser. No. 07/707,412 filed on 28 May 1991, now abandoned, which is a continuation application of Ser. No. 07/417,171 filed on 4 Oct. 1989, now abandoned, which is a continuation application of Ser. No. 06/898,272 filed on 20 Aug. 1986, now abandoned, which is a continuation-in-part application of Ser. No. 06/754,507 filed on 12 Jul. 1985, now abandoned, and a continuation-in-part application of Ser. No. 06/881,311 filed on 2 Jul. 1986, now abandoned, which is a continuation-in-part application of Ser. No. 06/677,156 filed on 3 Dec. 1984, now abandoned, which is a continuation-in-part application of Ser. No. 06/627,959 filed on 5 Jul. 1984, now abandoned, which applications are incorporated herein by reference.

This invention relates to the therapy of inflammatory, particularly immune-potentiated inflammatory events. In particular, it relates to the use of tumor necrosis factor antagonists for the suppression of graft rejections (of or by the host), and for the treatment of arthritis, systemic lupus, Crohn's disease and other autoimmune or inflammatory disorders.

The application of recombinant DNA techniques has resulted in the production of highly purified recombinant human tumor necrosis factor-alpha (rTNF-$\alpha$) and -beta (rTNF-$\beta$). These factors share amino acid sequence homology and show similarities in many of their biologic functions.

Tumor necrosis factors (TNFs) originally were identified by their ability to target tumor cells in vitro and in vivo for cytolysis or growth inhibition. Much of the interest attending the discoveries of these uses was based on their differential cytotoxicity. While TNFs will directly lyse many types of tumor cells, they have generally been considered to be relatively innocuous for normal untransformed, non-virally infected adult cells.

TNF-$\alpha$ has been said to have a central role in the immune response (Gamble et al., 1985, "Proc. Natl. Acad. Sci. USA" 82: 8667), but the nature of that role remains clouded. Both rHuTNF-$\alpha$ and $\beta$ activate human polymorphonuclear neutrophil functions in vitro (Shalaby et al., 1985, "J. Immunol." 135 : 2069–2073; Gamble et al., Id.) and rHuTNF-$\alpha$ modulates the function of endothelial cells in vitro (Stolpen et al., 1986, "Am. J. Pathol." 123: 16; Nawroth et al., 1986, "J. Exp. Med." 163: 740). See also Ezekowitz et al., "J. Clin. Invest." 76: 2368 (1985), Lommitzer et al., "Clin. Exp. Immunol." 29: 501 (1977), and Cross et al., "Infect. Immun." 22: 502 (1978). Also, recent studies showed the capacity of rHuTNF-$\alpha$ to act as an endogenous pyrogen and to induce interleukin-1 (IL-1) (Dinarello et al., 1986, "J. Exp. Med." 163: 1433 and Nawroth et al., 1986, "J. Exp. Med." 163: 1363).

On the other hand, Broxmeyer et al., "J. Immun." 136(2): 4487 (1986) reported that TNF-$\alpha$ and TNF (LuKII) suppress in vitro colony formation by human bone marrow granulocyte-macrophage, erythroid and multipotential progenitor cells. The immunosuppressive effect of TNF (LuKII) and TNF-$\alpha$ was inhibited, respectively, by polyclonal anti-human TNF(LuKII) and monoclonal anti-recombinant human TNF-$\alpha$. Similarly, Murphy et al. suggested that activated T cells regulate hematopoiesis through the release of inhibitory as well as stimulatory factors, and that the simultaneous production of IFN-$\gamma$ and lymphotoxin (TNF-$\alpha$) may represent a mechanism of suppression of hematopoiesis ("J. Exp. Med." 164: 263, July 1986). See also Degliantoni et al., "J. Exp. Med." 162: 1512 (1985). Fujisawa et al. have reported that immunosuppression by monocytes from patients with tuberculosis is associated with increased production of IL-1 ("Am. Rev. Respir. Dis." 133: 73 (1986), and it has been believed in certain quarters that IL-1 is a mediator of immunosuppression (Wallis et al.). In any case, little is known that would correlate the in vitro effects of HuTNF-$\alpha$ and -$\beta$ to the roles of these factors in the complex matrix of the immune inflammatory response in vivo.

Transplantation immunology has advanced on two fronts. In one respect, research has been directed towards the development of host immunosuppressive drugs such as cyclosporin antibiotics and steroids. Such drugs exert extensive and undesirable side effects. Other research has concentrated on the use of monoclonal antibodies to target lymphocyte subsets involved in transplant rejection. Since antibodies are directed against an entire lymphocyte subset they are not focused on any principal mediator of immune inflammatory response. Their activity, like that of cyclosporins and steroids, therefore, is relatively nonspecific. It would be best if immunosuppressive agents were targeted against an effector or mediator rather than an entire cell subset since the subset may be involved in desirable mechanisms of the immune response.

A substance(s) identified as "lymphotoxin" has been postulated to be involved in or to be a mediator of delayed type hypersensitivity. For example, "lymphotoxin" is released by the peripheral blood lymphocytes of polymyositis patients when incubated in vitro with autochthonous muscle tissue in vitro (Johnson et al., 1972 "J. Clin. Invest." 51: 2435) and has been found in rejecting allografts (Lowry et al., 1985, "Transplantation" 40(2): 183–188). It has been postulated that "lymphotoxin" and gamma interferon may have synergistic deleterious effects on the integrity of transplanted tissues. However, it also was recognized that other potent macromolecular toxins are released by NK cells, cytotoxic T cells and macrophages, and their potential role in delayed type hypersensitivity and tissue injury remain to be elucidated (Lowry et al., Id.)

"Lymphotoxin" also was reported to be released by sensitized T lymphocytes from myocardial infarct patients exhibiting delayed type hypersensitivity to myoglobin (Mirrakhimov et al., 1985, "Ter Arkh." 56(10): 53–56).

"Lymphotoxin" has been postulated to be induced in abnormally high quantities in infected T cells by the trans acting protein of human immunodeficiency virus. These abnormally high quantities are proposed to result in immunosuppression and T cell self-destruction (Ruddle, 1986, "Immunology Today" 7: 8–9).

Korsmeyer et al., "Clin. Immun. and Immunopathology" 5: 67–73 (1976) disclosed data consistent with the hypothesis that naturally occurring anti-lymphocyte antibodies in systemic lupus erythematosus (SLE) are a secondary manifestation of a suppressor cell defect with possible specificity for nonsuppressor T-cell subpopulations such as helper or killer cells, a view consistent with the report that anti-thymocyte antibodies were capable of limiting allograft rejection (Gelford et al., 1974, "J. Immunol. 113:1) and thus may be more specific for helper or killer cell functions. See also Terasaki et al., "New Engl. J. Med." 283(14): 724 (1970) wherein anti-lymphocytic antibodies in the sera of SLE and arthritis patients were referred to as "lymphotoxin". For the role of lymphocytotoxic antibodies in inflammatory bowel disease see Strickland et al., "Clin. Exp. Immunol." 21: 384–394 (1975).

Two classes of nonacidic drugs used to treat arthritis and other inflammatory diseases were found to inhibit lysis of murine L cells by PHA-P induced human lymphocyte cytotoxins, but the acidic anti-inflammatory compounds salicylate and phenylbutazone gave little protection against the cytotoxin (Peter, 1971, "Cell. Immunol." 2: 199–202). The cytotoxin(s) were characterized as having an approximate molecular weight of 80,000 d. In this regard see Peter et al., "Arthritis Rheum." 14:179 (1971), who report the isolation of cytotoxins from synovial fluid. It is difficult to square any postulatable role for lymphocyte cytotoxins in view of recent reports that gamma-interferon ameliorates arthritis in cancer patients. Gamma-interferon is known to act synergistically with TNF-β and TNF-α in antiviral and antiproliferative assays.

Other quandaries exist in the arthritis field. For example, research has been directed at drugs that block interleukin-1, presumably in order to suppress immune function, while other workers have suggested administering interleukin-2, despite its immunopotentiating action, because of indications that arthritis patients are deficient in interleukin-2 ("Wall Street Journal", Jul. 28, 1986).

In summary, a variety of tentative and hypothetical postulates exist for the mechanisms underlying various. immune-mediated inflammatory responses. Many of the postulates are mutually inconsistent and most are based on observations which cannot distinguish cause from epiphenomenology.

Accordingly, it is an object herein to provide compositions that are in fact capable of precisely targeting acute immune inflammatory responses without producing significant undesirable side effects.

This and other objects will be apparent from consideration of the specification as a whole.

SUMMARY

The objects of this invention are-accomplished by a method comprising administering to a patient with an inflammatory condition a therapeutically effective amount of an antagonist for TNF-α and/or TNF-β. It is not necessary to administer an interferon antagonist, nor to use other immunosuppressive substances in the course of therapy. The method herein is particularly useful in suppressing graft versus host and host versus graft rejections in organ transplants, the former including in particular bone marrow transplants. Preferably, the antagonist is a TNF-α antagonist.

DETAILED DESCRIPTION

For convenience, the term TNF collectively shall mean tumor necrosis factor-α or -β from animals or humans, together with naturally occurring alleles thereof. TNF-α is described by Pennica et al. "Nature" 312: 721 (1984). TNF-β, also referred to as lymphotoxin, is described by Gray et al. "Nature" 12: 724 (1984).

The novel compositions for use herein are TNF antagonists. These substances function in one of two ways. First, antagonists will bind to or sequester the TNF molecule itself with sufficient affinity and specificity to substantially neutralize the TNF epitopes responsible for TNF receptor binding (hereinafter termed sequestering antagonists). Alternatively, TNF antagonists will compete with native TNF for the cell surface receptor or intracellular site to which TNF binds in the course of cell lysis (hereinafter termed competitive antagonists). Both groups of antagonists are useful, either alone or together, in the therapy of immunoinflammatory responses.

Sequestering antagonists include TNF cell surface receptors and neutralizing antibodies to TNF. TNF-α neutralizing antibodies are readily raised in animals such as rabbits or mice by immunization with TNF-α in Freund's adjuvant followed by boosters as required. Immunized mice are particularly useful for providing sources of B cells for the manufacture of hybridomas, which in turn are cultured to produce large quantities of inexpensive anti-TNF-α monoclonal antibodies. Surprisingly, murine monoclonal antibodies have been obtained that exhibit high anti-TNF-α activity, on the order of $10^{10}$ liters/mole. TNF-β neutralizing antibodies are prepared by the method described in European patent application 168,214.

TNF receptors are obtained by first identifying a cell line obtained from the species to be treated with the antagonist that is cytolysed by TNF. Examples of suitable receptor sources include ME-180 and, for TNF-α receptors only, placenta. The cells are cultured (if cell lines), lysed, cell membranes recovered by centrifugation, the membranes extracted with detergent (preferably Triton X-100) and the protein in the membrane extract dialyzed free of detergent. Since both TNF-α and TNF-β are capable of binding a common receptor, this receptor may be purified by affinity binding with either TNF-α or TNF-β and is suitable for neutralizing either factor. Preferably, the receptors are further purified by immunoprecipitation with murine neutralizing monoclonal antibody, rabbit anti-mouse antibody and polyethylene glycol, followed by redissolution and separation on nondenaturing gel electrophoresis.

The receptor preparations also are useful for immunizing animals in conventional fashion to raise anti-receptor antibodies that are capable of inhibiting the binding of TNF to its receptor. These will be screened for in the same routine fashion as are TNF competitive antagonists.

Monoclonal and polyclonal anti-TNF antibodies suitable for use herein may vary widely in their affinity for TNF and their ability to neutralize TNF. Deficiencies in affinity or capacity on the part of the antibody can be made up by dosage increases. Acceptable polyclonal antibody should be capable of neutralizing greater than about 400 TNF units/μl, ordinarily greater than about 900 units (with TNF containing about $10^8$ units/mg of purified TNF). Polyclonal rabbit antisera will neutralize about 900 units/ml. Murine monoclonal anti-TNF-α antibodies have been obtained that neutralize 2700 and 2300 units of TNF-α/μg, respectively, when purified by conventional methods using ammonium sulfate fractionation followed by DEAE sepharose column chromatography. Two neutralizing epitopes for TNF-α have been identified. One of these, the D/E epitope is the most prevalent by far. The other epitope, the B epitope, is quite rare.

Polyclonal antisera from immunized animals or monoclonal antibodies in hybridoma culture are harvested by techniques known per se and purified to the desired degree. Typically, the immunoglobulin fraction is separated from the antisera or hybridoma culture supernatants by conventional methods, for example ethanol or polyethylene glycol fractionation. Preferably the antibodies are of the IgG class, although other classes such as IgM are acceptable. Further, the anti-TNF antibodies alternatively are provided as monovalent subunits such as Fab fragments containing the TNF-binding variable region. Such subunits will exhibit less side effects, e.g. immunogenicity, than intact antibodies containing constant regions. Methods are well-known per se for the preparation of Fab fragments from intact antibodies.

Competitive TNF antagonists preferably are TNF antagonistic variants. Such variants include substitutions, deletions or insertions of residues (amino acid sequence variants) as well as other covalent modifications, e.g. alkylated TNF. However, amino acid sequence variants are most preferred as they are readily manufactured in recombinant cell culture and recovered as chemically uniform, homogeneous compositions. Further, covalent modifications are more likely to immunize the patient against TNF, an event that is undesirable from the standpoint of long term patient recovery.

Antagonistic TNF amino acid sequence variants are variants of the mature TNF amino acid sequence that are capable of inhibiting TNF cytotoxic activity, but which have substantially no cytotoxic activity of their own. Antagonistic TNF sequence variants will competitively bind to cell surface receptors or intracellular TNF recognition sites without exerting any substantial cytotoxic effect, thereby displacing TNF or preventing TNF from binding to or interacting with the cells.

Antagonistic TNF sequence variants are characterized by amino acid deletions, substitutions and/or insertions which lead to the substantial inactivation of TNF cytotoxic activity without substantially interfering with the ability of the antagonist to inhibit TNF cytotoxic activity. Typically, deletional mutations are preferred as they are less likely to induce an active anti-TNF immune response in patients to whom the antagonists are administered.

The sites within the human TNF-α molecule that are selected for sequence variation generally are located within about residues 10 to 66, 113 to 134 and 150 to 157 (numbered following Pennica et al., Id.) Residues within these regions are believed to be important for TNF-α cytotoxic activity. Since an amino terminal domain within about residues 1 to 40 is believed to be externalized and therefore likely to be involved in receptor binding, non-cytotoxic analogues that are capable of competing with endogenous TNF-α generally will be mutated at points in the C-terminal direction from this region. Deletions, substitutions or insertions of disparate residues in these regions (40–66, 110–134 and 150–157) are anticipated to yield TNF variants having reduced or no cytotoxic activity combined with varying degrees of antagonist activity. Those mutants having the optimum combination of antagonist activity and reduced cytotoxicity are identified by the screening assays described above.

Sites within the human TNF-β molecule that are preferred for mutation generally are located within about residues 28–37, 46–55, 65–81, 136–149 and 166–171 (numbered following Gray et al., Id.). More detailed specific embodiments are set forth below.

In the process of making TNF amino acid sequence variants, existing residues in the native TNF molecule will be substituted by or flanked by inserted residues that are unlike those found at the site of substitution or insertion. Residues characterized as unlike are those for example which bear a substantially different charge or affinity for water than the residue which is substituted or adjacent to which an insertion is made. For example, amino acid residues in the following groups are substituted for one another or inserted adjacent to residues from different groups. Hydrophobic residues are methionyl, phenylalanyl, glycyl, valyl, leucyl and isoleucyl. Hydrophilic, uncharged amino acids include tyrosinyl, seryl and threonyl. Negatively charged residues include glutamyl or aspartyl, while basic residues are represented by lysyl, hydroxylysyl, arginyl and histidyl. Heterocyclic residues are tryptophanyl, prolyl and hydroxyprolyl. In accordance with this invention, residues from any one of these groups are substituted for or inserted adjacent to a residue from any other group in order to produce candidate variants.

TNF antagonists are easily identified and rated by routine screening of candidates for their effect on the activity of native TNF on susceptible cell lines in vitro. For example, the conventional L-cell assay for TNF activity is employed with a standard cell-lytic TNF formulation containing varying dilutions of candidate antagonist, e.g. from 0.1 to 1000 times the molar amount of TNF used in the assay, and controls with no TNF or no-antagonist. The amount of TNF activity, in units, neutralized by the antagonist candidate will be recorded as the antagonizing titer in vitro.

In more detail, TNF antagonists are identified as follows. First, the candidate substances are screened for TNF antagonist activity in a modification of a standard in vitro TNF cytotoxicity assay (Aggarwal et al., 1984, *Thymic Hormones & Lymphokines*. Goldstein. Ed. Plenum Publishing. p. 235). Target cells, generally a publicly available TNF-susceptible murine L-929 cell line or a susceptible human cell line, are seeded into microtiter wells and grown to confluence. Serial dilutions in culture medium of the candidate together with a standard cytotoxic quantity of TNF are incubated at 37° C. for 16 hrs. and then pipetted into the wells. The cells are incubated to the point that the TNF controls demonstrate cytotoxic effect on at least 50% of the cells. Thereafter, the test wells are observed and scored for the proportion of protected cells. This is a measure of the ability of the candidate to block TNF cytotoxicity. TNF cytotoxicity is identified for example by failure of treated cells to take up stain (crystal violet) or by their release of an isotope such as $Cr^{51}$. Large numbers of candidate substances and dilutions are readily screened by automatic equipment, e.g. the Microelisa autoreader (Dynatech). Controls containing candidate alone are useful for determining the residual cytotoxic activity of competitive-type antagonists.

An initial in vivo screening procedure is recommended whereby the TNF antagonists identified in the in vitro assay are assayed for the same activity in an in vivo context. The preferred assay is a modification of the Meth A sarcoma model of E. Carswell et al., "Proc. Nat. Acad. Sci." 72:3666–3670 (1975). Briefly, this modified assay is carried out by growing Meth A sarcoma cells ($5 \times 10^5$ cells) in $CB6F_1$ female mice $(BALB/c \times C57BL/6)F_1$ for 7–10 days. The tumors that develop are injected with serial dilutions of a preincubated solution containing TNF and a candidate substance as described above. After 24 hours, mice are sacrificed by cervical dislocation, tumors removed and necrosis scored histologically. Candidates that reduce or inhibit the necrotic activity of TNF on the sarcomas are selected for further screening.

The first step in the screening procedure (the in vitro cell culture screen) can be omitted but the efficiency of identifying effective antagonists will be lowered correspondingly. The third step in the TNF antagonist screening procedure comprises determining the activity of the antagonist in a known animal model. For example, serial dilutions of the candidate are administered to mice prior to or at points in time after bone marrow transplantation, after which suppression of the graft versus and the host rejection by the transplanted marrow monitored, for example by following splenomegaly. This is useful in confirming antagonist activity in vivo as well as for determining suitable dosages. Alternatively, the murine collagen-induced arthritis model is

7 suitable for screening activity and determining effective doses for each candidate.

Inflammatory or immune-potentiated inflammatory events to be treated with TNF antagonists are characterized by the presence of a humoral and/or cellular response directed against an undesired foreign or self target tissue or by uncertain etiology. Typically, immune potentiating inflammatory events are characterized by antibodies directed against host tissue by way of an aberrant host response, host antibodies against grafted tissue, or antibodies of graft origin directed against host tissue. Such events also are characterized by infiltration of polymorphonuclear neutrophils and mononuclear leukocytes into the target tissue, pain, localized edema, possible vascular endothelial injury and excessive production of cytokines by stimulated cells. Other than in transplantation immunity, such events occur during the course of diseases including arthritis, systemic lupus. Crohn's disease, and other autoimmune disorders known to those skilled in the art, and frequently in inflammatory conditions such as sarcoidosis or vasculitis.

The therapeutically effective amounts of TNF antagonist will be a function of many variables, including the type of antagonist, e.g. whether TNF sequestering or competitive, the affinity of the antagonist for TNF, any residual cytotoxic activity exhibited by competitive antagonists, the route of administration, the clinical condition of the patient (including the desirability of maintaining a non-toxic level of endogenous TNF activity), the presence of multiple TNF combining sites in sequestering agents, e.g. antibodies, and whether or not the antagonist is to be used for the prophylaxis or for the treatment of acute rejection episodes. Since the maximum tolerated dose of TNF-α in human clinical trials has ranged up to about 25 µg/m²/24 hrs, the amount of antagonist administered generally need not exceed a dose which is calculated to neutralize this amount of TNF-α. Accordingly, the molar dose of TNF antagonist will vary about from 0.001 to 10 times the maximum tolerated molar dose of TNF-α, although as noted above this will be subject to a great deal of therapeutic discretion. It is to be expected that concentrations of TNF localized at the sites of inflammation may exceed the whole body maximum therapeutic dose. Assay of the TNF concentration in inflammatory infiltrates will provide guidance as to the amount of TNF antagonist to be employed, particularly if localized administration is practical, e.g. in Crohn's disease (suppositories) or arthritis (injections into synovial fluid). Similar dosages and considerations apply in the case of TNF-β. The key factor in selecting an appropriate dose is the result obtained: If the patient's inflammatory response does not at least partially resolve within about 48 hours after administration, the dose should be gradually elevated until the desired effect is achieved. Correspondingly higher doses of polyclonal anti-TNF having a lower titer of TNF neutralizing activity and/or lower affinity for TNF will be required, and vice versa for antibody preparations with greater affinity and titer. Also, relatively higher doses will be initially needed for the treatment for acute rejection or inflammatory episodes, i.e., for patients in acute organ transplant rejection or undergoing arthritic flares.

In view of the therapeutic urgency attendant acute rejection episodes, the TNF antagonist should be intravenously infused or introduced at the inflammatory lesion immediately upon the development of symptoms or serological evidence of TNF activity. However, prophylaxis is suitably accomplished by intramuscular or subcutaneous administration.

The TNF antagonist is administered in conjunction with other anti-inflammatory agents used in or proposed for the treatment of individual immunoinflammatory conditions as appropriate, e.g. gold colloids, cyclosporin antibiotics, salicylate and corticosteroids (such as methylprednisolone). However, when employed together with TNF antagonists these agents may be employed in lesser dosages than when used alone.

The following examples are to be construed as merely illustrative of the invention and not as limiting its scope. All citations herein are expressly incorporated by reference.

EXAMPLE 1

Preparation of Neutralizing Antibody to Human TNF-α

Human TNF-α was synthesized in recombinant culture by the method of Pennica et al. (op cit.) or isolated from cultured induced HL60 cells or peripheral blood lymphocytes. A BALB/c mouse (#185) was injected with human TNF-α immunogens on the following immunization schedule:

| Day | Administration Route | Immunogen |
| --- | --- | --- |
| 1. | subcutaneous (sc) | 0.5. ml of 30,000 units TNF-α from human peripheral blood lymphocytes in PBS + 0.5 ml Freund's complete adjuvant. |
|  | intraperitoneal (ip) | 0.5 ml of 30,000 units TNF-α from peripheral blood lymphocytes in PBS. |
| 15. | half sc., half intramuscular (im) | $5 \times 10^4$ units TNF-α on 1.64% alum |
| 43. | half sc., half im. | 10 mg E. coli recombinant human TNF-α on 0.1 ml 1.64% alum. |
| 49. | intravenous (iv) | 50 µl of 1.3 mg/ml recombinant TNF-α. |
| 74. | sc | 50 µl of 2.5 mg/ml recombinant TNF-α + 100 µl Freund's complete adjuvant. |
| 81. | iv | 2 µg recombinant TNF-α. |
| 84. | ip | 200 µg recombinant TNF-α. |
| 85. | ip | 400 µg recombinant TNF-α (10 µg iv). |
| 86. | ip | 400 µg recombinant TNF-α (10 µg iv). |
| 87 | ip | 400 µg recombinant TNF-α. |

The anti-TNF-α neutralizing titer increased only gradually throughout the immunizations to day 74. The "Barragen" procedure conducted on days 81–87 ("J. Imm. Meth." 32: 297–304, 1980) reduced serum titer but increased the population of antigen-reactive cells, thereby greatly increasing the efficiency of the subsequent fusion procedure in producing useful clones. Retrospectively, only several alum-TNF-α immunizations are believed to be needed before the Barrage procedure in order to obtain satisfactory titers.

On day 88 the spleen from mouse 185 was harvested, disrupted and the spleen cells fused with P 3×63-Ag8.653 (ATCC CRL 1580) cells using the PEG fusion procedure of S. Fazekas de St. Groth et al., "J. Imm. Meth." 35: 1–21 (1980). The fused culture was seeded into 480 microtiter wells and cultured in conventional manner. The anti-TNF-α activity of culture supernatants was determined by adding a sample of the supernatant to microtiter wells precoated with recombinant human TNF-α, incubated, washed, horseradish peroxidase labelled-goat anti-mouse IgG added to the wells, incubated, washed and the bound HRP activity determined. 51 of the 480 wells contained clones making anti-TNF-α. Of these, 14 stable fusions which secreted anti-TNF-α were selected.

IgG purified from anti-TNF-α containing culture supernatants by ammonium sulfate precipitation and DEAE column chromatography was mixed with a solution of TNF-α in PBS, and incubated for 16 hours at 37° C. in order to ensure maximal binding. The incubation mixture was then assayed using the L cell cytotoxicity assay (Aggarwal et al., infra). The neutralizing titer is expressed as the number of TNF units in the cytotoxicity assay that are neutralized per μl of unpurified antiserum or hybridoma supernatant culture medium. 10 cultures of the 14 produced neutralizing antibodies. Of the 10, TNF-αD (IgG$_1$) exhibited an affinity of $10^{10}$ liters/mole and neutralizing titer of 2700 units/μg, TNF-αE (IgG$_1$), $10^{10}$ liters/mole and a titer of 2300 units/μg and TNF-αB, $10^9$ liters/mole and per μg neutralized 80% of 4074 TNF-α units. The D and E types are apparently directed at substantially the same TNF-α epitope because they compete for TNF-α binding. The B type competes at about the 50% level for the D/E epitope, thus suggesting that it is specific for its own unique epitope. TNF-αB was obtained from a single hybridoma (Genentech deposit no. 15-3-5E3H3).

Rabbit polyclonal antisera were obtained by immunizing New Zealand white rabbits with 0.6 mg TNF-α/0.5 ml PBS+1.5 ml of Freund's Complete adjuvant (FCA) sc on day 1, 125 μg TNF-α/0.125 ml PBS+375 μg FCA sc on day 36 and 125 μg TNF-α/0.5 ml PBS+1.5 ml FCA sc about 2 months later. Antisera harvested after the final booster contained a neutralizing titer of about 900 units/μl.

EXAMPLE 2

Preparation of TNF-α and TNF-β Antagonist Analogues

The following M13 mutagenesis method, based on J. Adelman et al., "DNA" 2(3): 183–193, is generally applicable to the construction and expression of any TNF DNA sequences encoding antagonist TNF sequence variants. Additional information relating to M13 mutagenesis is provided by U.K. patent application 2,130,219A. Other methods suitable for creating TNF analogues are known to those in the art. For example, mutant DNA is constructed by simply chemically synthesizing the entire sequence or by synthesizing a portion of the sequence and ligating the fragment into the remainder of the required DNA. Chemical DNA synthesis is advantageous when the artisan wishes to prepare the mutant directly without first obtaining from natural sources the DNA encoding tumor necrosis factor. Ordinarily, however, the starting DNA will encode the natural amino acid sequence, including its allelic variants.

In order to avoid redundancy, representative contemplated sequence variants of TNF-α are illustrated in which Trp 28 or 114 is converted to phenylalanine or tyrosine (substitutions), Val 150 through Leu 157 or Lys 11 through Arg 31, inclusive, is deleted (deletions) and Ser-Ser-Ser is inserted after Phe 152 or Leu 26 (insertions). Other TNF-α variants which are representative candidates include Δala$_4$ his$_{15}$, Δleu$_{55}$ tyr$_{56}$, tyr$_{59}$→ile, gln$_{61}$→trp, gly121→pro, phe$_{124}$→ser, gly$_{129}$→pro, arg$_{131}$→asp, leu$_{132}$→trp, and ala$_{134}$→tyr. It should be understood, however, that other variants of TNF-α or TNF-β are generated in the same general fashion.

Contemplated sequence variants of TNF-β fall within residues 28–37, 46–55, 65–81, 136–149 and 166–171 (numbered as in Gray et al., Id.). Preferably, only one of the sequences 28–34, 51–54, 65–81 and 143–149 is varied. For example, representative embodiments include Δlys$_{28}$-his$_{32}$, Δarg$_{51}$-leu$_{54}$, Δleu$_{65}$-pro$_{68}$, Δile$_{72}$-val$_{75}$, Δval$_{75}$-val$_{79}$, Δgln$_{78}$-phe$_{81}$, Δala$_{137}$-gln$_{140}$, Δasp$_{130}$-ser$_{148}$, lys$_{28}$→thr, lys$_{28}$→asp, ala$_{30}$→lys, ala$_{31}$→asp, his$_{32}$→tyr, arg$_{50}$→glu, ala$_{51}$→tyr, phe$_{53}$→lys, leu$_{54}$→his, leu$_{66}$→tyr, tyr$_{73}$→lys, tyr$_{76}$→lys, gln$_{78}$→tyr, phe$_{81}$→ser, gln$_{140}$→tyr, leu$_{141}$→trp, asp$_{130}$→phe, gln$_{131}$→leu, ser$_{148}$→asp, ala$_{170}$→tyr, pro$_{29}$ pro ala$_{30}$, tyr$_{73}$ tyr phe$_{74}$, ser$_{77}$ ser gln$_{78}$, and asp$_{145}$ asp gln$_{146}$. Each substitution or variation at a given site in TNF-α may be made in TNF-β, and vice versa, at the corresponding residue as shown in FIG. 4 of Pennica et al., Id. In addition, other substitutions at any of the representative sites set forth above are suitable for generating candidate variants.

Identification of operative and optimal embodiments is straight-forward. Routinely, one dilutes preparations of each variant in a constant amount of TNF-α or TNF-β having cytotoxic activity and then assays the formulations in the conventional L-929 assay, screening for a reduction cell lytic activity upon an increase in relative proportion of candidate variant.

It will be appreciated that even if a candidate antagonist fails to exert antagonistic activity it will remain useful as an antitumor agent if it retains cytotoxic activity, or as a standard or labelled reagent for immunoassay of native TNF so long as it retains at least one cross-reacting immune epitope.

It is desirable in preparing DNA encoding variant TNF derivatives that no codon changes be made which create the opportunity for mRNA transcribed therefrom to form high energy (arithmetically greater than about −15 kcal/mole) stem-and-loop structures. Avoidance of DNA that is transcribed into mRNA containing such structures will generally result in higher yields. In addition, transformant host-preferred codons should be employed to enhance translational efficiency.

Suitable starting DNA for TNF-α variants is the EcoRI-HindIII fragment of pTNFTrp (Pennica et al., op cit.) obtained by sequential digestion with EcoRI and HindIII, followed by isolation of the TNF-α gene-containing fragment. This fragment includes the trp promoter and structural gene for methionyl-tumor necrosis factor-α. To obtain a single-stranded copy of this gene suitable for mutagenesis, the EcoRI-HindIII fragment is cloned into the polylinker site of phage M13 mp8 RF-DNA (J. Messing et al., 1982, "Gene" 19: 269–276; "RF" means the replicative form of the phage; this phage is commercially available). An aliquot of the EcoRI-HindIII digestion mixture is added to a ligation reaction containing 10 ng of M13 mp8 RF-DNA which had been digested previously with EcoRI and HindIII. After incubation at room temperature for 2 hrs, the ligation mixture is used to transform *E. coli* JM103 (a commercially available strain; JM101 can also be used). Transformed cells are plated with top agar containing X-GAL (dibromo-dichloro-indolyl-galactoside) and IPTG (isopropylthiogalactoside). Bacterial cultures (1 ml) infected with phage picked from colorless plaques are used to isolate M13 mp8/TNF RF-DNA by a miniscreen procedure (Birnboim and Doly, 1980, "Nuc. Acids Res." 7:1513–1523). The resulting recombinant phage M13 mp8/TNF carries the coding strand for the TNF-α gene.

For site-directed mutagenesis, oligodeoxyribonucleotides (mutagenesis oligomers) are synthesized with a sequence complementary to stretches of 15 bases on either side of the mutation site as shown in the following diagrams, wherein N indicates complementary bases and M indicates the nucleic acid to be inserted, deleted or substituted. Insertions or deletions should be made in groups of 3 in order to retain the downstream portion of the gene in phase.

| For deletions: | oligomer DNA | $(N)_{15}$ $(N)_{15}$ |
|---|---|---|
| | vector DNA | $(N)_{15}$ (M) $(N)_{15}$ |
| For substitutions: | oligomer DNA | $(N)_{15}$ $(M_1)$ $(N)_{15}$ |
| | vector DNA | $(N)_{15}$ $(M_2)$ $(N)_{15}$ |
| For insertions: | oligomer DNA | $(N)_{15}$ (M) $(N)_{15}$ |
| | vector DNA | $(N)_{15}$ $(N)_{15}$ |

$M_1$ indicates a base or an oligomer which is not complementary to the base or oligomer $M_2$. Here, $M_1$ is the desired mutant sequence. Ordinarily, oligomers are also prepared that act to make more than one type of mutation at a time.

The antisense oligomer for the exemplary mutants are as shown in the following Table:

single-stranded M13 mp8 DNA (about 10,000 plaque-forming units) yields less than 100 plaques in a DNA transformation assay, whereas the same amount of RF-DNA, retains more than 80 percent of its transforming properties. S1-treated DNA is used to transform E. coli JM103 and the resulting phage analyzed by in situ plaque screening.

Bacterial plates (15-cm diameter) containing several hundred recombinant M13 phage plaques are screened by in situ plaque hybridization (Benton et al., 1977, "Science" 196: 180–182) for both the parental and the mutated genotype using the appropriate labelled oligomers on separate sets of filters (about $10^6$ cpm per filter). Hybridization is overnight at 50° C., 40 percent formamide, 5×SSC. Filters are washed at 45° C., 2×SSC, 0.02 percent sodium dodecyl sulfate,

| TNF-α Analogue | Primer |
|---|---|
| Trp 28 –> Phe 28 | PGGC CCG GCG GTT CAG AAA CTG GAG CTG CCC CTC OH |
| Trp 114 –> Tyr 114 | PATA GAT GGG CTC ATA GTA GGG CTT GGC CTC AGC OH |
| ΔVal 150 - Leu 157 | PGTT GGA TGT TCG TCC TCC TCA CTG CCC AGA CTC GGC OH |
| ΔLys 11 - Arg 31 | PGAG GGC ATT GGC CCG GTC ACT CGG GGT TCG OH |
| Phe$_{152}$ Ser Ser Ser Gly$_{153}$ | PCAG GGC AAT GAT CCC ACT ACT ACT AAA GTA GAC CTG CCC OH |
| Leu$_{26}$ Ser Ser Ser Gln$_{27}$ | PGCG GTT CAG CCA CTG ACT ACT ACT GAG CTG CCC CTC AGC OH |

These primers are synthesized by conventional methods. For use in the mutagenesis procedure, 10 pmoles of the oligomers or lac primer 5'-CTTTTCCCAGTCACGAC-3' are each phosphorylated for 30 min at 37° C. in 10 μl of 50 mM Tris-HCl (pH 7.5) containing 0.1 mMEDTA, 10 mM MgCl$_2$, 10 mM dithiothreitol, 0.1 mM ATP and 2 U of T4 polynucleotide kinase. For use as probes (see infra), 2 pmoles of the synthetic oligonucleotides are phosphorylated as above except that 0.1 mM ATP was supplemented with 1 μM γ-$^{32}$p ATP (Amersham). Specific activities are routinely higher than 5×10$^6$ cpm/pmole of oligonucleotide chain.

Hybridization of each oligomer and the lac primer to the single-stranded DNA from phage M13 mp8/TNF, followed by primer extension, results in the formation of partial heteroduplex DNAs, one strand of which contains the DNA.

For partial heteroduplex formation, single-stranded M13 mp8/TNF DNA (300 ng) is heated to 80° C. (2 min), 50° C., (5 min), and room temperature (5 min) in 20 μl 10 mM Tris-HCl (pH 7.5), 0.1 mM EDTA, 50 mM NaCl, containing 1 pmole each of phosphorylated oligomer and primer (added as aliquots from the kinase reaction). Primer extension is started by the addition of 30 μl 50 mM Tris-HCl (pH 8.0), 0.1 mM EDTA, 12 mM MgCl$_2$, 10 mM dithiothreitol, 0.7 mM ATP, 0.07 mM dATP, 0.2 mM each of dGTP, dTTP, dCTP, and containing 2 U E. coli DNA polymerase I, large fragment and 20 U T4 DNA ligase. After 30 min at room temperature, reaction mixtures are incubated for 4 hr at 37° C. followed by overnight incubation at 4° C. Aliquots are phenol extracted and DNA is precipitated with ethanol and dissolved in 15 μl of water. DNA in these aliquots is used to transform E. coli JM103.

The lac primer hybridizes to the phage at a location 5, to the oligomer. Primer elongation stabilizes the heteroduplex structure. The oligomer and primer are enzymatically phosphorylated to allow the T4 DNA ligase to join connecting DNA chains.

Phenol extracted heteroduplex DNA from aliquot C (10 μl) is added to 10 μl 0.06M Na-acetate pH 4.5, 0.6M NaCl, 0.6 mM ZnCl$_2$, and containing 200 U S1 nuclease. After incubation at 37° C. for 5 min, yeast tRNA (5 μg) is added and nucleic acids are recovered by phenol extraction and ethanol precipitation. Using the same S$_1$ conditions, 30 ng of air-dried, and exposed to X-ray film at −70° C. using an intensifying screen.

It will be necessary to vary the stringency of the hybridization procedure (by altering the concentration of SSC) in order to resolve the hybridization of oligomer to the mutant DNA strand (a perfect complement) as opposed to hybridization to the starting DNA; each mutant will vary in its ability to hybridize depending upon the nature and number of bases substituted, deleted or inserted. For example, detecting a mutation in a single base will require high stringency conditions to discriminate between mutant and unmutated parental DNA where the mutation is minor, e.g. deletion of a codon or substitution of 1–3 bases, the hybridization probe should be smaller than the mutating oligomer. Typically this will be a probe of about 14 to 20 bases. The task of screening mutant deletions is facilitated by the use of a probe containing or constituting the deleted sequence to assay for loss of the sequence. If this probe fails to hybridize to DNA from a selected plaque one can conclude that the desired loss of the target sequence has occurred.

A plaque that hybridizes with the labelled oligomer is picked and inoculated into E. coli JM103. Single-stranded (ss) DNA is prepared from the supernatant and double-stranded (ds) DNA is prepared from the cell pellet. The ssDNA is used as a template for the dideoxy sequencing of the clone using the M13 universal primer or a synthetic oligomer complementary sequences located 3' of the mutated region of the tumor necrosis factor DNA. Dideoxy sequencing confirms that the recovered plaque contains the mutant DNA. Such phage is designated M13 mp8/TNFmtnt.

M13 mp8/TNFmtnt is digested with EcoRI and HindIII and the TNF variant-encoding fragment recovered. pTrpTNF is digested with EcoRI and HindIII and the vector fragment recovered. The fragment encoding the variant is then ligated to the vector fragment and the ligation mixture used to transform E. coli W3110, NL106, or 294 (ATCC 31446). The variant TNF is recovered by gel electrophoresis. A comparison of this gel with that obtained upon the parallel electrophoresis and staining of pTNFtrp-transformed E. coli protein shows a band migrating at approximately 17,000 daltons representing the variant protein. The amino acid sequence of the purified variant is confirmed. Residual cytotoxicity of the analogue is determined in the TNF cytotoxicity assay. Substantially non-cytotoxic analogues are assayed for antagonist activity by TNF composition as described above. Analogues that contain less than about 10% of the cytotoxic activity of TNF on a molar basis and which are able to neutralize at least about 20% of TNF cytotoxic activity on a molar basis are selected for analysis in in vivo experimental models.

EXAMPLE 3

Use of Neutralizing TNF-α Antibody to Suppress Mixed Lymphocyte Reaction

In the following study, human TNF-α and TNF-β were obtained in >98% purity from recombinant cell culture (rHuTNF-α and β) rHuTNF-α was mature and contained $7.6 \times 10^7$ U/mg protein as determined by the L cell assay described in Aggarwal et al., 1984, *Thymic Hormones & Lymphokines*, Goldstein, Ed. Plenum Publishing p. 235. The rHuTNF-β formulation was of approximately the same purity and was assayed in the same fashion. rHuTNF-β was the unglycosylated $His_{24}$ N-terminal species. Rabbit polyclonal anti-rHuTNF-α antisera was obtained as described in Example 1. Blood drawn from healthy donors was heparinized, diluted with an equal volume of saline, layered on Ficoll-Hypaque gradients (Sp. gr. 1.08) which were centrifuged at 400×g for 40 min. at room temperature. PMBC (peripheral blood mononuclear cell) isolated at the plasma-Ficoll interface were separated and washed three times in cold Hank's balanced salt solution (Grand Island Biological Co., Grand Island N.Y., (Gibco)). The final cell pellet was resuspended in complete medium and counted. Cell viability was ≧95 percent as determined by trypan blue exclusion. RPMI 1640 medium (Gibco) was supplemented with 10 percent heat-inactivated pooled human AB serum (Peninsula Memorial Blood Bank, S. San Francisco, Calif.), 2 mM L-glutamine, 0.1 mM non-essential amino acids, 10 mM Hepes buffer (Gibco), 5 µg/ml garamicin (Schering Corp., Kenilworth, N.J.) 500 U/ml penicillin, 500 µg/ml streptomycin (Gibco) and $5 \times 10^{-5}$ M β-mercaptoethanol (complete medium).

Mixed Lymphocyte Cultures

The proliferative response of the PBMC to allogeneic stimulation was determined in the one-way mixed-lymphocyte reaction (MLR) performed in replicates in microtiter plates as detailed previously (Shalaby et al., 1983, "Cell. Immunol." 82:269). Briefly, $10^5$ responder cells in 200 µl of complete medium were co-cultured with either mitomycin C treated autologous cells (control cultures) or mitomycin C treated allogeneic cells (stimulated cultures) in replicates of three to six cultures. The treatment of PBMC with mitomycin C (Sigma Chemical Co., St. Louis, Mo.) was accomplished as described previously (Shalaby et al., 1983, "Cell Immunol." 82:269). Lymphokine effects were tested in cultures prepared in parallel. Cultures were incubated for 7 days. Six hr prior to harvesting, the cultures were pulsed with 2 µCi/well of [$^3$H]-thymidine (40–60 Ci/mmol) (Amersham, Arlington Heights, Ill.) and processed with a multiple automated sample harvester onto glass-fiber discs. The discs were allowed to dry and [$^3$H]-thymidine incorporation was determined using a Beckman scintillation spectrometer Model LS6800. Data were calculated as net counts per min (cpm) (mean cpm stimulated cultures minus mean cpm control cultures). Consistently, the mean $^3$H-thymidine incorporated by control cultures was $\geq 1.5 \times 10^3$ cpm. Statistical analysis was performed using the paired-comparison (one-sample) student t test.

PBMC responder cells were incubated with mitomycin C-treated allogeneic cells in the absence (control) or presence of 1000 U/ml of recombinant human IFN-α 2/1, rTNF-α or rTNF-β. $^3$H-Thymidine incorporation was determined after seven days of incubation. Data are presented as mean cpm of 4–6 cultures ± SE. The cpm of responders incubated with autologous stimulators were 2500 cpm or less.

TABLE 1

The effect of rHuIFNα2/1, rHuTNF-α, and rHuTNF-β on the proliferative response in MLR.

| Culture Condition | $^3$H-thymidine incorporated (Cpm × $10^{-3}$ 4 ± SE) | | | |
|---|---|---|---|---|
| | Exp. 1 | Exp. 2 | Exp. 3 | Exp. 4 |
| Control | 76 ± 6 | 17 ± 3 | 30 ± 4 | 9 ± 2 |
| rHuIFN-α2/1 | 4 ± 1 | 2 ± 0.3 | 22 ± 4 | 2 ± 0.4 |
| rHuTNF-α | 97 ± 5 | 31 ± 2 | 108 ± 10 | 60 ± 10 |
| rHuTNF-β | 87 ± 3 | 42 ± 5 | 56 ± 8 | 37 ± 5 |

Other studies in which rHuTNF-α and rHuTNF-β were added to the PBMC cultures at different times after the start of incubation with allogeneic cells demonstrated that rHuTNF-α produced maximal $^3$H-thymidine incorporation only when added at the time the cultures were established, whereas rHuTNF-β produced no change in enhancement whether added at 0, 3, 4 or 5 days of incubation. At day 6 no effect was observed. It was apparent that rHuTNF-α and rHuTNF-β were enhancing the proliferative response of PMBC to an antigenic stimulus and that suppression of this response would be useful in suppressing undesirable immune inflammatory conditions. In order to determine whether a rHuTNF antagonist would function in suppression of PMBC proliferation, additional experiments were performed using specific rabbit antibodies against rHuTNF-α. Aliquots of rHuTNF-α(1000 U/ml) were incubated in media only or in media containing either specific polyclonal antisera adequate for the neutralization of 1000 U rHuTNF-α or normal rabbit serum used at a final dilution similar to that for the neutralizing antiserum. After 2 h of incubation at 37° C., these aliquots (at the same dilution) were added to MLR cultures at desired concentrations and also tested in the L cell bioassay to confirm the neutralization of rHuTNF-α cytotoxic activity. The results of (Exp. 1, Table 2 below) demonstrate that rHuTNF-α which had been neutralized with antibodies failed to cause an enhancement of MLR, unlike the phenomenon observed when unneutralized rHuTNF-α alone was added to cultures. The presence of specific antibodies alone did not influence the reaction in this particular experiment (Exp. 1, Table 2).

TABLE 2

The specificity of rHuTNF-α induced effect and the impairment of proliferative activities by rabbit antibodies against rHuTNF-α.

| Culture Condition | $^3$H-thymidine incorporated (Cpm × $10^{-3}$ 4 ± SE) | | | | |
|---|---|---|---|---|---|
| | Exp. 1 | Exp. 2 | Exp. 3 | Exp. 4 | Exp. 5 |
| Control | 21 ± 3 | 14 ± 1 | 40 ± 10 | 20 ± 1 | 138 ± 26 |
| rHuTNF-α | 86 ± 8 | 27 ± 2 | 64 ± 8 | 79 ± 14 | 173 ± 11 |
| Ab + rHuTNF-α | 31 ± 5 | 16 ± 3 | 0.5 | 0.5 | 69 ± 11 |
| Ab only | 15 ± 8 | 1.2 | 0.5 | 1.5. | 71 ± 6 |
| NRS | 48 ± 7 | 12 ± 3 | N.D.* | N.D.* | 143 ± 11 |

*Not determined

In repeat experiments, it was noticed that the addition of antibodies against rHuTNF-α to cultures of MLR in some cases completely abolished $^3$H-thymidine incorporation (Exp. 2, 3, and 4, Table 2) or caused a 50 percent inhibition of the reaction (Exp. 5, Table 2). These results raised the possibility that antibodies against rHuTNF-α may interfere with the synthesis of lymphokine(s) e.g., interleukin-1 (IL-1) and IL-2, that regulate the proliferative activities of responder cells in MLR (Muller, G. (ed) Immunol. Rev. 51, 1980). To test this hypothesis, cultures of MLR were established with and without the addition of 1000 U/ml rHuTNF-α, or specific antibodies. After 24 h of incubation, supernatants were collected and tested for IL-1 activity by the murine thymocyte assay (Mizel, 1981, In: *Manual of Macrophage Methodology*, Herscowitz et al., Eds.). The results of these experiments demonstrated supernatants of rHuTNF-α treated cultures contain an increased level of IL-1 activity and that the addition of specific antibodies against rHuTNF-α causes a 40–60 percent suppression of IL-1 activity in MLR supernatants.

EXAMPLE 4

Suppression of Graft versus Host Reaction In Vivo by Administration of Anti-rHuTNF-α

The purpose of this study was to investigate the influence of administered rMuTNF-α and rabbit antibodies (RbAb) against rMuTNF-α on the development of graft-vs-host reaction (GVHR) in newborn randomly sexed $BDF_1$ mice. The results of preliminary experiments indicate that the administration of rMuTNF-α can further enhance GVHR and, conversely, the administration of RbAb decreases the severity of GVHR as determined by the Simonsen spleen weight assay. (Simonsen, M. et al., 1959, In: *Biological Problems of Grafting*, F. Albert et al., editors Charles C. Thomas, Publisher, Springfield, Ill. 214).

The cloning and expression in *E. coli* of the cDNA for murine TNF-α have been reported (Pennica, D., et al., Proc. Natl. Acad. Sci. 88: 6060, 1985). The materials used were purified to greater than 98 percent purity. Titers of recombinant murine TNF-α(rMuTNF-α) were calculated on the basis of its cytotoxic activities as determined by the L cell bioassay (Aggarwal, op cit) and showed a specific activity of $7-8 \times 10^7$ U/mg protein. Polyclonal antibodies against rMuTNF-α were generated in rabbits immunized with purified preparations of rMuTNF-α substantially as shown in Example 1 (Nedwin G. E. et al., J. Immunol. 135: 2492, 1985) and had a neutralization titer of $2.5 \times 10^6$ U/ml as determined by bioassay results of neutralized rMuTNF-α activity.

Newborn $BDF_1$ (C57BL/6×DBA/2) litters with C57BL/6 (B6) mothers purchased from Simonsen laboratories (Gilroy, Calif.) were used. Nursing mothers were allowed access to Purina lab chow and water ad libitum and the newborns were put on study in 24–48 h of birth.

GVHR was measured by the Simonsen spleen weight assay op cit. Adult $BDF_1$ and B6 spleens were made into a single cell suspension by teasing in Hanks balanced salt solution (HBSS). The red blood cells were lysed by hypotonic shock followed by centrifugation. Spleen cell pellets were suspended in HBSS, counted, and adjusted at the desired concentration. Spleen cells were injected intraperitoneally into 24–48 hrs. old BDF1 newborns in the following experiments. The various groups of newborns were litters injected with HBSS, litters injected with adult syngeneic $BDF_1$ spleen cells, litters injected with adult semiallogeneic B6 spleen cells, litters injected with either of the spleen cells in combination with rMuTNF-α or antibodies against rMuTNF-α and litters injected with rMuTNF-α or antibodies only. The protocol for each litter consisted of the i.p. injection of about $2.5 \times 10^6$ spleen cells. The amount of rMuTNF-α was 2000 units per animal administered in 0.1 ml of HBSS. The amount of rabbit antisera used (unfractionated) contained 2000 neutralizing units of antibodies against rMuTNF-α, this being diluted into 0.1 ml of HBSS for injection. A 2000 neutralizing unit dosage of antisera was mixed with spleen cells and then immediately injected. Then the same dose (2000 neutralizing units) was administered by i.p injection (without spleen cells) on days 1, 2, 3, 5 and 8. On day 10 all animals were sacrificed and their spleens examined. The animals weighed about 3½–6 grams upon sacrifice, but their weight increased rapidly during the 10 days of the study due to normal growth. Thus, a suitable intraperitoneal dose in this experiment ranged from about $0.25 \times 10^6$ to about $3 \times 10^6$ neutralizing units/Kg/24 hours.

Spleen indices were calculated (Klein, J. and Park, J. M., J. Exp. Med. 137: 1213, 1973) and the data are expressed as mean spleen indices (MSI) which was obtained by averaging the spleen indices of at least 6 mice in each group.

In an initial experiment we tested the number of adult spleen cells required for the induction of GVHR in newborns. The results indicated that $2.5 \times 10^6$ cells were adequate for causing a GVHR and that the severity of the reaction was only slightly increased by injection of an intermediate or a higher number of cells ($10-25 \times 10^6$ cells). The results of five independent experiments, summarized in Table 3, show that enhancement of GVHR by rMuTNF-α injection was not observed consistently (marked enhancement in Exp. 2, and only a slight enhancement in Exp. 3, Table 3). However, a consistent suppression of GVHR was observed in mice receiving injections of antibodies against rMuTNF-α(Exp. 1,4, and 5, Table 3). Rabbit anti-rMuTNF-α or rMuTNF-α injected in the absence of exposure to B6 cells had no effect.

TABLE 3

The Influence of rMuTNF-α and Antibodies against rMuTNF-α on GVHR

| Treatment | Mean Spleen Indexes | | | | |
|---|---|---|---|---|---|
| | Exp. 1 | Exp. 2 | Exp. 3 | Exp. 4 | Exp. 5 |
| HBSS | 0.53 | 0.43 | 0.52 | ND | ND |
| rMuTNF-α | 0.48 | 0.54 | ND | ND | ND |
| $BDF_1$ cells | 0.45 | 0.47 | 0.44 | 0.53 | 0.52 |
| B6 cells | 1.51 | 1.12 | 1.36 | 1.86 | 2.19 |
| B6 cells + rMuTNF-α | 1.50 | 1.41 | 1.50 | 1.85 | ND |
| B6 cells + Antibodies | 1.17 | ND | ND | 1.39 | 1.29 |

ND = Not determined

We claim:

1. A tumor necrosis factor-alpha (TNF-alpha) antagonist comprising an antibody which neutralizes cytotoxic activity of human TNF-alpha.

2. The TNF-alpha antagonist of claim 1 wherein said antibody comprises a monoclonal antibody.

3. The TNF-alpha antagonist of claim 2 wherein said monoclonal antibody is an IgG antibody.

4. The TNF-alpha antagonist of claim 2 wherein sad monoclonal antiody is an IgM antibody.

5. The TNF-alpha antagonist of claim 1 wherein said antibody comprises a murine antibody.

6. The TNF-alpha antagonist of claim 1 wherein said antibody comprises a rabbit antibody.

7. The TNF-alpha antagonist of claim 1 wherein said antibody comprises a monovalent antibody.

8. The TNF-alpha antagonist of claim 7 wherein said monovalent antibody comprises a fab fragment containing a variable region of the antibody.

9. A TNF-alpha antagonist comprising an anti-TNF-alpha antibody which blocks cytotoxic activity of human TNF-alpha.

10. A TNF-alpha antagonist comprising a monoclonal antibody which neutralizes cytotoxic activity of human TNF-alpha, wherein said antibody is generated using a human TNF-alpha protein which, when in a purified form, migrates as a single band on a SDS-PAGE gel to a molecular weight of about 17,000 daltons.

11. A TNF-alpha antagonist consisting of a monoclonal anti-TNF-alpha antibody which blocks cytotoxic activity of TNF-alpha on murine L-929 cells in vitro.

12. A composition comprising the TNF-alpha antagonist of claim 1 and an isotonic carrier.

13. A composition comprising the TNF-alpha antagonist of claim 9 and an isotonic carrier.

14. A composition comprising the TNF-alpha antagonist of claim 10 and an isotonic carrier.

15. A composition comprising the TNF-alpha antagonist of claim 11 and an isotonic carrier.

* * * * *

UNITED STATES PATENT AND TRADEMARK OFFICE
CERTIFICATE OF CORRECTION

PATENT NO. : 5,795,967

DATED : AUGUST 18, 1998

INVENTOR(S): AGGARWAL ET AL.

It is certified that error appears in the above-identified patent and that said Letters Patent is hereby corrected as shown below:

In [63], line 9, before "Ser. No. 881,311" insert —a continuation-in-part application of—.

In column 3, line 42, "are-accomplished" should read —are accomplished—.

In column 3, line 59, "12:" should read —312:—.

In column 4, line 44, "antibody" should read —antibodies—.

In column 8, line 42, "Barragen" should read —Barrage—.

In column 11, line 28, "CTTTTCCCAGTCACGAC-3'" should read —GTTTTCCCAGTCACGAC-3'—.

In column 15, line 31, "CDNA" should read —cDNA—.

In column 15, line 58, "BDF1" should read —$BDF_1$—.

In column 16, line 55 (claim 4), "sad" should read —said—.

In column 16, line 56 (claim 4), "antiody" should read —antibody—.

UNITED STATES PATENT AND TRADEMARK OFFICE
CERTIFICATE OF CORRECTION

PATENT NO. : 5,795,967
DATED : AUGUST 18, 1998
INVENTOR(S) : AGGARWAL ET AL.

It is certified that error appears in the above-identified patent and that said Letters Patent is hereby corrected as shown below:

In column 16, line 64 (claim 8), "fab" should read —Fab—.

Signed and Sealed this

Twentieth Day of April, 1999

Q. TODD DICKINSON

*Attest:*

*Attesting Officer*　　*Acting Commissioner of Patents and Trademarks*